United States Patent [19]

Percarpio

[11] Patent Number: 4,465,200
[45] Date of Patent: Aug. 14, 1984

[54] LOW CONTAMINATION CLOSURE FOR BLOOD COLLECTION TUBES

[75] Inventor: Edward P. Percarpio, N. Haledon, N.J.

[73] Assignee: Becton, Dickinson and Company, Paramus, N.J.

[21] Appl. No.: 501,744

[22] Filed: Jun. 6, 1983

[51] Int. Cl.³ .......................................... B65D 47/36
[52] U.S. Cl. ..................................... 215/247; 604/415
[58] Field of Search ...................... 215/247, 248, 249; 604/415

[56] References Cited

U.S. PATENT DOCUMENTS

| 1,413,703 | 4/1922 | Biehn | 215/247 |
| 3,017,050 | 1/1962 | Barr et al. | 215/247 |
| 3,460,702 | 8/1969 | Andrews | 215/247 |
| 3,974,930 | 8/1976 | Gizard et al. | 215/247 |
| 4,243,150 | 1/1981 | Gunne et al. | 215/247 |

FOREIGN PATENT DOCUMENTS 28411  5/1981  European Pat. Off. ............ 215/247

Primary Examiner—Donald F. Norton
Attorney, Agent, or Firm—Robert P. Grindle

[57] ABSTRACT

A composite closure arrangement is provided for blood sample collection tubes, and particularly evacuated blood collection tubes for reducing exposure of a technician to any blood droplets or blood aerosol during removal of a sample of the blood from the container. The device also hides and contains any such aerosol or droplets. Moreover, the device provides enhanced ease of removal of the stopper, when desired. A cap is configured to be placed over and fitted onto the rubber stopper of the tube, with the top portion of the cap extending over and spaced from the top of the stopper to define a cavity between the overlying portion of the cap and the top of the stopper. The center of the overlapping portion of the cap includes a sample needle access bore providing access to the stopper diaphragm. Cooperating opposed abutments on the cap and the stopper maintain the cap on the stopper.

5 Claims, 2 Drawing Figures

LOW CONTAMINATION CLOSURE FOR BLOOD COLLECTION TUBES

BACKGROUND AND DESCRIPTION OF THE INVENTION

This invention relates generally to a closure assembly for evacuated blood collection tubes such as VACUTAINER ® Brand evacuated tubes. More particularly, this invention relates to such a closure which reduces the incidence of contamination of the user of the evacuated tube when obtaining a blood sample from the tube.

As is well known in the medical field, evacuated tubes are used in large quantities to take blood samples from patients for subsequent testing of the blood for various purposes to determine if a patient has certain diseases or blood problems or other physical health problems of some kind. It is routine for a laboratory technician, for example, to take several samples from a single evacuated tube for various tests. Since the tube is evacuated, there is a pressure differential across the stopper holding the sample in the tube many times. Thus, when a needle is inserted through the diaphragm of the stopper, there can be an aerosol of the sample which may spray onto the technician. Moreover, when taking samples, sometimes blood droplets are left on the top surface of the stopper during the removal of the needle once a sample has been taken from the evacuated tube.

Thus, there is an exposure problem to the user of such evacuated tubes containing blood samples of contamination from a blood sample which may be a diseased blood sample of some kind.

With this invention, by contrast, an arrangement is provided for reducing to a minimum exposure of aerosol or blood droplets which may be evident in removing a blood sample from an evacuated tube. This is achieved by providing a cap assembly which is mounted over the resilient rubber stopper of the evacuated tube. The internal surface of the cap is configured to provide opposing abutments which cooperate with the portion of the rubber stopper extending from the evacuated tube in order to hold the cap in place. The cap includes a top portion which extends over the top of the stopper to define between the top surface of the stopper and the bottom surface of the extended top portion of the cap a cavity which serves to contain any blood droplets or aerosol which may arise when a sample is removed from the tube. The top portion extending over the top surface of the stopper includes a central bore for receiving the needle necessary for puncture of the diaphragm for removing the sample. Otherwise, the top surface of the stopper is effectively closed so as to, as discussed above, contain any aerosol or blood droplets which may arise from taking the sample.

With the foregoing and additional objects in view, this invention will now be described in more detail, and other objects and advantages thereof will be apparent from the following description, the accompanying drawings, and the appended claims.

DETAILED DESCRIPTION OF THE INVENTION

Figure 1:
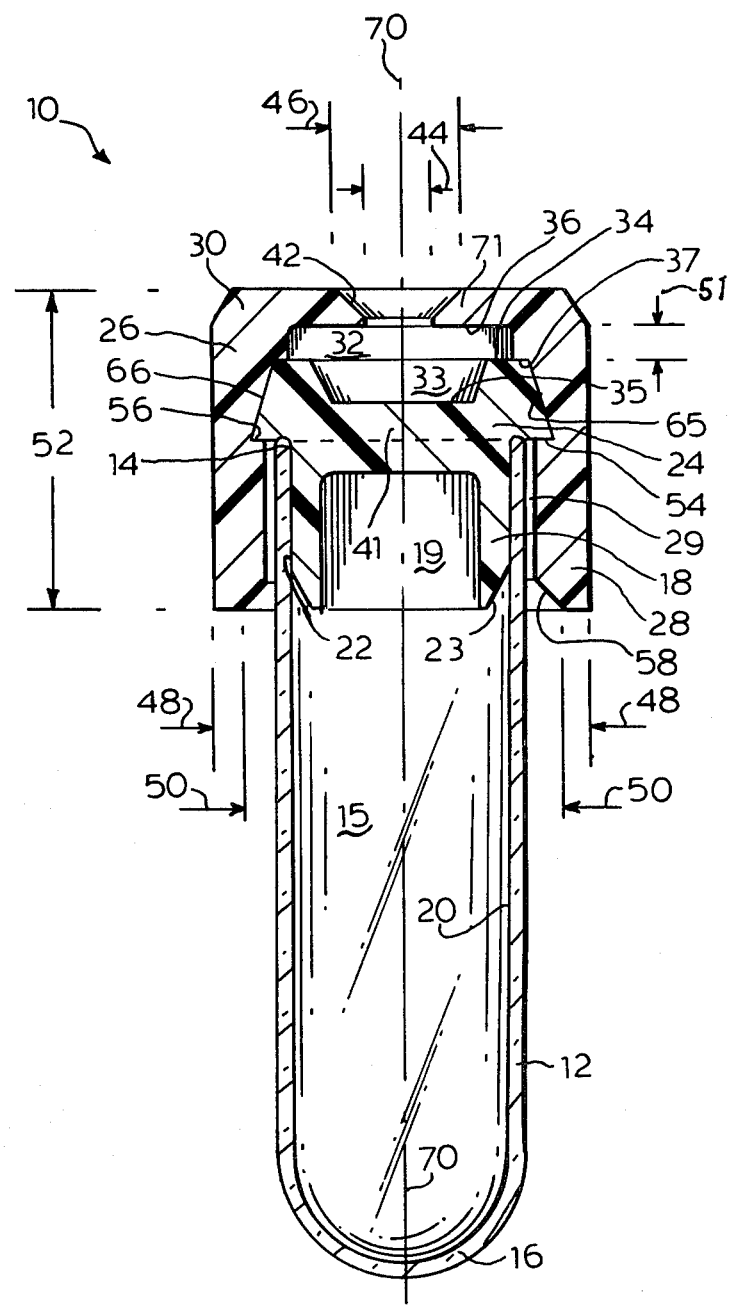
FIG. 1 is a longitudinal sectional view of a blood sample tube, which may be evacuated, with a composite closure assembly thereon illustrating the invention.

Referring to the drawings in which like reference characters refer to like parts throughout the several views thereof, in FIG. 1 a closure assembly generally designated 10 is shown placed on the open end 14 of tube 12. Tube 12 is a conventional blood sample tube which may be evacuated for receiving subsequently a blood sample therein. The tube has the open end 14 and a closed end 16. An elastomeric stopper 18 closes the open end 14 of the tube. Routinely, tube 12 will be evacuated during its manufacture and assembly for receiving, subsequently, a blood sample from a patient which sample is inserted through the thin diaphragm portion 41 of stopper 18. That is, stopper 18 includes an upper well 33 in the top surface 35 thereof and a lower well 19. These opposed wells serve to define a thin diaphragm portion 41 through which a blood sample needle may be inserted for introducing a blood sample into the internal chamber 15 of tube 12. Subsequent to the insertion of a blood sample into tube 12, which may have been taken by a doctor or a technician from a patient suffering from a particular illness, the tube is forwarded to a laboratory routinely for examination of the blood sample. The technician reintroduces a needle through diaphragm 41 for removing at least a portion of the blood sample. When this takes place, many times, because of residual pressure differentials across the stopper 18, there will be an aerosol of the blood sample around the area adjacent the needle passing through diaphragm 41. Moreover, when the needle is removed from diaphragm 41, many times blood droplets will be left on the top surface 35 of the diaphragm 41. These aerosol or droplet portions of the blood sample may contaminate the technician and it is the purpose of this invention to protect technicians from such contamination by incorporating the cap assembly 10 including the cap 30 in combination with the stopper 18.

In describing stopper 18 in more detail, stopper 18 includes an upper flange portion 24 which has an abutment lower surface 54 thereon which extends beyond the opening of the open end 14 of tube 12. Also, stopper 18 includes a depending annular portion, as shown in FIG. 1 which provides an annular outer sealing surface 22 which cooperates with the internal surface 20 of tube 12 to provide sealing of tube 12 to contain the vacuum therein when the assembly is made for subsequent taking of blood samples. Cap 30 includes an annular depending portion with an internal tapered groove 65 which cooperates with the tapered outer surface 66 of the upper flange portion 24 of stopper 18. The tapered groove 65 tapers away from the axis 70 of the assembly and ends in an abutment surface 56 which cooperates with the overhanging bottom surface 54 of the tapered upper flange portion 24 of the stopper 18. These cooperating surfaces serve to maintain the cap assembly 30 fixed in place on stopper 18. In addition, the opposed top surface 34 of stopper 18 and surface 37 on cap 30 serve this purpose.

Figure 2:
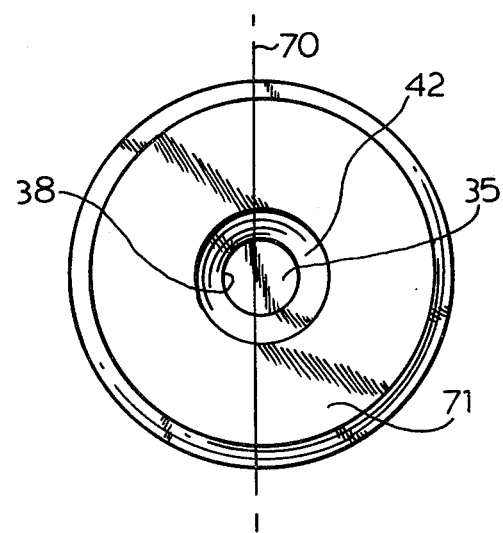
FIG. 2 is a top plan view of the apparatus of FIG. 1.

As can be seen in FIG. 1, cap 30 includes an upper annular portion 71 which overhangs the top surface 35 of well 33 for defining a cavity 32 between the lower surface 36 of this overhang portion of cap 30 and the surface 35 of well 33. As can be seen further in FIG. 1, the overhang portion includes a bore 38 for receiving a needle therethrough for engaging and passing through diaphragm 41 for inserting and removing blood samples from the container. Bore 38 includes a tapered entry portion 42 tapering toward or converging toward axis 70 for enhancing or guiding the operator's needle in passing through bore 38 to diaphragm 41. The relationship of the taper 42 and bore 38 are shown clearly in the plan view of FIG. 2.

The lower annular portion 28 of cap 30 is spaced as shown at 29 from the outer surface of tube 12 so that the cap 30 itself does not prevent rapid and easy removal of stopper 18, when desired, from tube 12. The operator need merely grasp the cap 30 which has a larger grasping surface for this purpose, to pry off the elastomeric stopper 18 from tube 12. The lower annular portion 28 of cap 30 includes a tapered annular surface 58 diverging away from axis 30, as shown in FIG. 1. This tapered surface serves to cooperate with the tapered surface 66 on the flange portion 24 of the stopper 18 to cam the annular portion 28 over the stopper for the initial assembly of the closure assembly 10. Of course, once the annular lower portion 28 of cap 30 has passed over the outer edge of flange 24, it snaps into place into firm engagement with stopper 18, as shown in FIG. 1. In this connection, cap 30 may be comprised of any generally flexible material such as a thermoplastic moldable material including, for example, polyethylene. It will be understood, however, that the cap may be comprised of other semi-rigid flexible materials such as metal or hard rubber.

While the dimensions of cap assembly 10 will vary, depending upon the size of the evacuated tube for which it is functioning as a closure, representative dimensions are as follows: The dimension 48 defining the width of flange 24 on stopper 18 is 0.686 inches. The cap 30 diameter will be about 0.78 inches to cooperate with a stopper of this dimension. The height 52 of cap 30 will be 0.72 inches, the bore 38 diameter 44 will be 0.05 inches, height 51 will be 0.05 inches and the tapered opening dimension 46 will be 0.125 inches. It is to be understood, however, that these dimensions are being presented as exemplary only and changes can be made, depending upon the dimensions of a particular evacuated tube being closed, as will be understood by practitioners-in-the-art.

Thus, when the composite assembly of stopper 18 and cap 30 are formed, then the composite assembly may be mounted on the top of tube 12 and inserted in the open end 14 thereof for sealing tube 12. In order to enhance the insertion of the lower annular portion of stopper 18, the lower surface thereof is tapered at 23 to enhance this insertion procedure.

Thus, there is provided, in accordance with this invention, a new composite closure assembly for evacuated tubes for taking blood samples which closure assembly is more hygienic to the user and the patient in that lower contamination from blood is contained within the assembly itself reducing exposure of a technician to aerosol caused by stopper removal or blood sample removal and blood droplets on the top of the stopper surface. The assembly herein serves to contain the small portions of a blood sample not ordinarily contained for reducing contamination, as will be understood. Moreover, the cap assembly herein is more readily removable from an evacuated tube because it provides a larger gripping surface and a certain flexibility for grasping and removing the stopper from the sealing engagement thereof with an evacuated tube. It should be understood, moreover, that during this removal procedure, the lower annular portion 28 of cap 30 serves to protect the technician from any blood which might escape from the open end 14 of tube 12 during this removal procedure.

As is apparent from the foregoing, the arrangements of apparatus provided in accordance herewith are readily and simply manufactured by mass production techniques in conventional molding procedures and the parts may be simply assembled and mounted on evacuated tubes with a limited amount of effort.

While the apparatus herein disclosed forms preferred embodiments of this invention, this invention is not limited to this specific apparatus, and changes can be made therein without departing from the scope of this invention which is defined in the appended claims.

What is claimed is:

1. A closure assembly for evacuatable tubes for receiving samples of body fluids comprising:
   (a) an annular stopper body with an upper integral annular flange portion, and a lower annular skirt portion;
   (b) an upper well in the top surface of said stopper body;
   (c) a lower well in the bottom surface of said stopper body, said lower well being defined by said skirt portion;
   (d) said upper and lower wells being coaxial with the axis of said stopper body to define a needle receiving diaphragm wall therein;
   the improvement characterized by
   (e) a flexible cap body for mounting on said annular stopper body,
   (f) said cap body having an open end and a closed end;
   (g) said open end having a well therein for receiving said stopper body;
   (h) said closed end having a needle receiving bore in the top surface thereof;
   (i) cooperating opposed annular abutment means on said stopper body and said cap body for maintaining said cap body on said stopper body; and
   (j) said closed end of said cap body being spaced from the opposed top surface of said stopper body to define a sample containing chamber therein.

2. The assembly of claim 1, further characterized by
   (a) said annular flange of said stopper body and the end wall of said open end of said cap body having cooperating tapered surfaces; and
   (b) said cooperating tapered surfaces providing camming action upon mounting said cap body on said stopper body.

3. The assembly of claim 1, further characterized by said cooperating opposed annular abutment means comprising
   (a) the upper and lower surfaces of said upper annular flange portion of said stopper body;
   (b) the outer surface of said flange portion including a tapered surface converging toward the upper surface of said stopper body;
   (c) a tapered annular groove in the well of the open end of said cap body for receiving said flange portion of said stopper body;
   (d) said tapered annular groove converging toward the said closed end of said cap body;
   (e) said tapered annular groove including an upper and a lower surface defining opposed abutment surfaces; and
   (f) the said upper and lower surfaces of said flange portion defining cooperating abutment surfaces with the said upper and lower surfaces of said tapered annular groove.

4. The assembly of claim 1, further characterized by
 (a) an elongated evacuatable container having a closed end and an open end;
 (b) said open end receiving said lower annular skirt portion in sealing engagement therein;
 (c) said open end of said cap body extending around and spaced from the portion of said evacuatable container adjacent the open end thereof.

5. The assembly of claim 4, further characterized by
 (a) the end surface of said lower annular skirt portion being tapered for easing the insertion thereof into said open end of said container.

* * * * *